United States Patent [19]

Banitt et al.

[11] 4,097,481

[45] Jun. 27, 1978

[54] TERTIARY AMIDE DERIVATIVES OF PYRROLIDINE AND PIPERIDINE

[75] Inventors: Elden H. Banitt, Woodbury, Minn.; William E. Coyne, Hudson, Wis.

[73] Assignee: Riker Laboratories, Inc., Northridge, Calif.

[21] Appl. No.: 739,613

[22] Filed: Nov. 8, 1976

[51] Int. Cl.² ............................................. C07D 211/32
[52] U.S. Cl. .......................... 260/293.77; 260/326.47; 260/293.86; 424/267; 424/274
[58] Field of Search ....................... 260/293.77, 326.47

[56] References Cited

U.S. PATENT DOCUMENTS 3,900,481    8/1975    Banitt et al. ..................... 260/293.77

FOREIGN PATENT DOCUMENTS 2,556,457    6/1976    Germany ........................ 260/293.77

*Primary Examiner*—Norma S. Milestone
*Attorney, Agent, or Firm*—Cruzan Alexander; Donald M. Sell; Donald C. Gipple

[57] ABSTRACT

Certain compounds in which a carbon atom of a pyrrolidine or piperidine ring is bonded directly or through a methylene group to the completely substituted nitrogen of a substituted benzamido group, and their pharmaceutically acceptable salts, are active antiarrhythmic agents.

2 Claims, No Drawings

TERTIARY AMIDE DERIVATIVES OF PYRROLIDINE AND PIPERIDINE

BACKGROUND OF THE INVENTION

This invention relates to certain compounds in which a carbon atom of a pyrrolidine or piperidine ring is bonded directly or through a methylene group to the nitrogen of a substituted benzamido group, and said nitrogen atom is substituted by a lower alkyl or cycloalkyl group, and their pharmaceutically acceptable salts. The benzamido group of these compounds is substituted by one to three 1,1-dihydroperfluoroalkoxy substituents. The compounds and their pharmaceutically acceptable salts are active as antiarrhythmic agents. The invention also relates to certain novel intermediates and to processes useful to prepare the compounds.

Esters of benzoic acid substituted on the aromatic ring by 1,1-dihydroperfluoroalkoxy substituents are described in U.S. Pat. No. 3,655,728. Certain amides of benzoic acid substituted on the aromatic ring by 1,1-dihydroperfluoroalkoxy substituents are described in U.S. Pat. No. 3,719,687. The novel compounds of the present invention differ structurally from those described in U.S. Pat. No. 3,719,687 in that (1) the compounds of the invention must have an asymmetric center, (2) the benzamido nitrogen atom of the compounds of the present invention is bonded to a carbon atom of the pyrrolidine or piperidine ring therein through a methylene group or carboncarbon bond, and (3) the compounds of the invention may be either secondary or tertiary amines. The compounds of the present invention have, in general, an improved therapeutic ratio over the compounds of the prior art.

Compounds of U.S. Pat. No. 3,900,481 are structurally similar to the compounds of the present invention, but they are exclusively secondary amides and differ from the compounds of the present invention in several ways. Thus, it has been found that (1) salts of the compounds of the present invention fail to fluoresce under ultraviolet light, (2) salts of compounds of the present invention have improved water solubility and consequently greater ease of formulation, (3) compounds of the invention have increased stability since they are less susceptible to both acid and base hydrolysis, and (4) compounds of the invention lack certain side effects of the compounds of the art.

DETAILED DESCRIPTION OF THE INVENTION

This invention relates to chemical compounds and their pharmaceutically acceptable salts, processes for using the compounds of the invention, pharmaceutical compositions containing the compounds, processes for the preparation of the compounds, and novel intermediates useful in the processes of the invention.

The compounds of the invention are broadly described as follows:

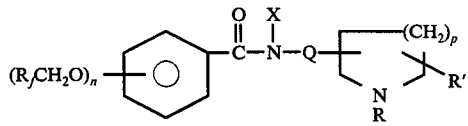

wherein $R_f$ is a perfluoroalkyl radical containing one to three carbon atoms ($C_mF_{2m+1}$ where $m$ is 1-3), n is one to three, p is one or two, Q is a carbon-nitrogen bond, methylene (—CH$_2$—), or methylmethylene (—CH(CH$_2$)—), X is lower alkyl or a cycloalkyl group containing five or six carbon atoms, and R and R' are hydrogen, methyl or ethyl and pharmaceutically acceptable salts thereof. The term "lower" whenever used herein relative to a substituent denotes a group containing from one to four carbon atoms.

Presently preferred are compounds of the invention wherein Q is (1) a carbon-nitrogen bond and is bonded to the 3 position of the pyrrolidine or piperidine ring or (2) a methylene or methylmethylene linking group and is bonded to the 2 position of the pyrrolidine or piperidine ring. Most preferably Q is methylene. Compounds wherein X contains one to three carbon atoms are also presently preferred. These classes of compounds are preferred because of generally greater antiarrhythmic potency as detected by animal tests.

Compounds of the invention wherein n is two, $R_f$ is $CF_3$ and the orientation of the dihydroperfluoroethoxy groups is 2,5 are also a presently preferred class as showing a high level of antiarrhythmic activity.

The compounds of the invention have at least one asymmetric carbon (the carbon atom of the pyrrolidine or piperidine ring to which the group Q is bonded) and can be resolved into optically active enantiomers by methods known to the art. In addition, other asymmetric centers are possible, e.g. when Q is methylmethylene or R' is methyl or ethyl. All of these optical isomers are included within the scope of the invention.

The compounds can be used directly or in the form of pharmaceutically acceptable acid-addition salts, especially as soluble acetic, hydrochloric, sulfuric or phosphoric acid salts. Other such salts include combinations with hydrobromic acid, sulfamic acid, methanesulfonic acid, benzenesulfonic acid, ethanedisulfonic acid, citric acid, maleic acid, oxalic acid, succinic acid, malic acid, fumaric acid, and tartaric acid. Pharmaceutically acceptable quartenary ammonium salts are also used, for example alkyl (especially lower alkyl) iodide and bromide salts.

The compounds of the invention are generally active as antiarrhythmics although both the activity (exhibited by the test methods presently available) and the therapeutic indices vary from compound to compound. The antiarrhythmic activity of compounds is manifested in their ability to block chloroforminduced ventricular fibrillation in mice, as demonstrated by the test procedure described in detail by J. W. Lawson, J. Pharmacol. Exp. Therap. 160:22-31, 1968.

Presently preferred compounds of the invention are:
2,5-bis(2,2,2-trifluoroethoxy)-N-n-butyl-N-(2-piperidylmethyl)benzamide,
2,5-bis(2,2,2-trifluoroethoxy)-N-methyl-[2-(6-methylpiperidyl)methyl]benzamide,
2,5-bis(2,2,2-trifluoroethoxy)-N-methyl-N-(2-piperidylmethyl)benzamide,
2,5-bis(2,2,2-trifluoroethoxy)-N-ethyl-N-(2-piperidylmethyl)benzamide,
2,5-bis(2,2,2-trifluoroethoxy)-N-ethyl-N-[2-(1-methylpyrrolidyl)methyl]benzamide,
2,5-bis(2,2,2-trifluoroethoxy)-N-cyclohexyl-N-(2-piperidylmethyl)benzamide,
and pharmaceutically acceptable salts thereof.

In clinical practice, the derivatives of the invention will be normally administered as antiarrhythmics orally or by injection in the form of pharmaceutical preparations comprising the active ingredient in the form of the free base or one of the common therapeutically acceptable salts, e.g. the acetate or hydrochloride, in association with a pharmaceutically acceptable carrier. The carrier may be a solid, semi-solid or liquid diluent or an ingestible capsule. Usually the active substance will comprise between 0.01 percent and 5 percent of preparations intended for injection and between 10 percent and 80 percent of preparations intended for oral administration. Particularly preferred for intravenous use are 0.05–1.0 percent aqueous solutions of the active compounds buffered with sodium acetate to pH of about 5–7 and, for oral use, 20–60 percent formulations of the active ingredient in mannitol, lactose or potato starch.

Pharmaceutical preparations in the form of dosage units for oral administration containing a compound of the invention in the form of the free base or a pharmaceutically acceptable acid addition salt may be prepared in various ways. The compounds may be mixed with a solid, pulverulent carrier, for example lactose, saccharose, sorbitol, mannitol, starches such as potato starch, corn starch or amylopectin, cellulose derivatives, gelatin. The carrier may also be a lubricant such as magnesium or calcium stearate, a Carbowax or other polyethylene glycol wax compressed to form tablets, or, preferably, cores which are then coated with a concentrated sugar solution which may contain, e.g. gum arabic, gelatin, talcum and/or titanium dioxide.

Ingestible capsules which may be used include hard or soft gelatin capsules.

Soft gelatin capsules (pearl-shaped closed capsules) and other closed capsules consist, for example, of a mixture of gelatin and glycerol, and contain, e.g. mixtures of the active substance with a vegetable oil, and hard gelatin capsules contain, for example, granulates of the active substance with solid, pulverulent carriers such as lactose, saccharose, sorbitol, mannitol; starches such as potato starch, corn starch, or amylopectin; cellulose derivatives or gelatin, as well as magnesium stearate or stearic acid.

For parenteral application by injection the preparations of the invention advantageously comprise an aqueous, generally saline, solution of a water-soluble, pharmaceutically-acceptable salt of the active substance and optionally also a stabilizing agent and/or a buffer substance, e.g. sodium acetate.

In addition, some of the compounds of the present invention exhibit activity as local anesthetics. These compounds can be administered by topical application to produce surface anesthesia and used to relieve itching, burning and surface pain or by local injection for surgical procedures. When they are administered topically the compounds are generally administered from aqueous solutions in pharmaceutical cream or salve bases, etc. When injected as anesthetics the compounds can be conveniently used as solutions, for example, in aqueous solutions which may be made isotonic, for example, by the addition of sodium chloride. The local anesthetic activity is observed using the corneal reflex test using rabbits as test animals. This test method is described by F. P. Luduena and J. O. Hoppe, J. Pharmacol. Ex. Therap., 104:40, 1952.

The compounds of the invention, other than those in which Q is a carbon-nitrogen bond connected to the 2 position of the heterocyclic ring, can be prepared by reacting a compound of the formula:

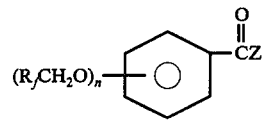

wherein Z is halogen, preferably chlorine, or a 1,1-dihydroperfluoroalkoxy group containing one to four carbon atoms, and R$_f$ and n are as defined hereinabove with an amine of the formula:

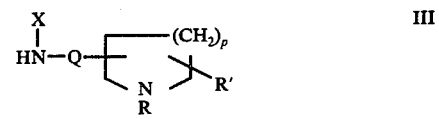

wherein X, Q, R, R' and p are as previously defined, except that when Q is in the 2 position it is not a carbon-nitrogen bond. The reaction is carried out in an inert solvent such as chloroform, benzene, glyme, toluene or diethyl ether. Preferably R is not hydrogen. An acid acceptor such as a tertiary amine is usually used when Z is halogen. The reaction temperature may be from 0° C. to the reflux temperature of the solvent. When Z is a 1,1-dihydroperfluoroalkoxy group, the reaction is generally carried out by refluxing the reactants without solvent or with an inert solvent such as glyme, followed by isolation of the product.

An alternative procedure which is generally useful, but particularly useful in the preparation of the compounds in which Q is a carbon-nitrogen bond in the 2 position, comprises reacting an amino- or aminomethylpyrrole or pyridine with a compound of Formula II and selectively reducing the resulting substituted pyridine or pyrrole derivative (IV) as follows:

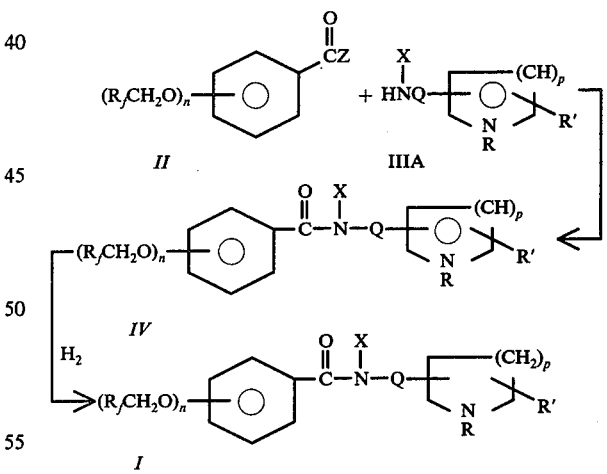

wherein X, R$_f$, n, Z, Q, p, R and R' are as previously defined, (Z being either halogen or 1,1-dihydroperfluoroalkoxy and Q being a carbon-nitrogen bond, methylene or methylmethylene), provided, however, that where the second reactant is a substituted pyridine (i.e p is 2), R in that compound and in the intermediate compound IV is not present (the valences of the nitrogen atom all being satisfied in the conjugated ring). This process, and the intermediate substituted pyridine and pyrroles (IV), are novel and form further aspects of the invention.

The intermediates (IV) are prepared using reaction conditions similar to those used in the previously described one-step process, depending upon whether Z is halogen or 1,1-dihydroperfluoroalkoxy. They are then reduced selectively using catalytic reduction to the corresponding piperidine and pyrrolidine derivatives of Formula I. The presently preferred catalyst for the catalytic reduction is platinum oxide. The reduction is generally run under acidic conditions, for example in acetic acid as solvent, in the presence of hydrogen chloride.

The compounds of Formula II can be conveniently prepared from the corresponding acids (that is, compounds of Formula II where Z is OH), said acids being known to the art. See, for example, U.S. Pat. No. 3,655,728. The compounds in which Z is halogen, e.g. chlorine, can be prepared by refluxing the acids with an excess of thionyl halide (chloride) in the presence of a small amount of dimethyl formamide. The excess thionyl halide is then removed by distillation. The compounds of Formula II in which Z is 1,1-dihydroperfluoroalkoxy are disclosed in U.S. Pat. No. 3,655,728 and can be prepared by reaction of the hydroxy and polyhydroxy aromatic acids with the alkylating agents of the formula:

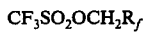

$$CF_3SO_2OCH_2R_f \qquad V$$

in the presence of sodium bicarbonate, potassium bicarbonate, or other metal bicarbonates in an inert solvent such as acetone. The resulting 1,1-dihydroperfluoroalkoxy-substituted aromatic ester can, in turn, be hydrolyzed to the free acid (compounds of Formula II wherein Z is OH).

The compounds of Formulae III and IIIA are generally known to the art, or can be conveniently prepared by methods known in the art. Thus compounds III can be prepared from the corresponding compounds IIIA by catalytic reduction. In addition, certain compounds of types III and IIIA can be prepared by reduction of the corresponding Schiff bases which are themselves prepared from the corresponding aldehydes by reaction with amines.

The following examples will more fully illustrate the preparation of the compositions of the invention. All temperatures in the examples given are in degrees Centigrade. Examples 1-11 relate to the preparation of intermediate compounds and the remaining examples relate to the preparation of compounds of the invention.

Example 1

To a stirred mixture of 4.08 g. (0.03 mole) of 2-(N-methylaminomethyl)-6-methylpyridine and 12.7 g. (0.12 mole) of sodium carbonate in 100 ml. of benzene is added over about 30 minutes 10.09 g. (0.03 mole) of 2,5-bis-(2,2,2-trifluoroethoxy)-benzoyl chloride in 40 ml. of benzene. After the completion of the addition, the mixture is heated to its reflux temperature and stirred and heated at reflux for about five hours.

The mixture is allowed to cool, then diethyl ether and water are added. The layers are separated, the organic layer is washed twice with saturated sodium chloride solution, then dried and finally evaporated under vacuum to provide a tan syrup. The syrup solidifies on standing and is recrystallized from a 2:1 hexane:benzene mixture (about 175 ml.), treating with decolorizing charcoal. The product is white crystals of 2,5-bis-(2,2,2-trifluoroethoxy)-N-methyl-N-[2-(6-methylpyridyl)-methyl]benzamide, m.p. 83°-86° C.

| Analysis: | %C | %H | %N |
|---|---|---|---|
| Calculated for $C_{19}H_{18}F_6N_2O_3$: | 52.3 | 4.2 | 6.4 |
| Found: | 52.3 | 4.0 | 6.3 |

Using the method of Example 1 the following compounds are prepared starting with 2,5-bis-(2,2,2-trifluoroethoxy)benzoyl chloride and selected secondary amines.

TABLE I

| Ex. No. | Starting Amine | Product | Melting Point (° C) |
|---|---|---|---|
| 2 | 2-(N-methylaminomethyl)pyridine | [structure: 2,5-bis(OCH$_2$CF$_3$)-benzamide with N-CH$_3$ and N-CH$_2$-(2-pyridyl)] | 81-91 |
| 3 | 2-(N-n-butylaminomethyl)pyridine | [structure: 2,5-bis(OCH$_2$CF$_3$)-benzamide with N-(CH$_2$)$_3$CH$_3$ and N-CH$_2$-(2-pyridyl)] | 82-84 |
| 4 | 2-(N-t-butylaminomethyl)pyridine | [structure: 2,5-bis(OCH$_2$CF$_3$)-benzamide with N-C(CH$_3$)$_3$ and N-CH$_2$-(2-pyridyl)] | 122-123.5 |

TABLE I-continued

| Ex. No. | Starting Amine | Product | Melting Point (° C) |
|---|---|---|---|
| 5 | 2-(N-cyclohexyl-aminomethyl)-pyridine | [structure: benzamide with cyclohexyl and pyridylmethyl on N, and two OCH₂CF₃ groups on benzene ring] | 113–114 |
| 6 | 2-(N-ethylamino-methyl)pyridine | [structure: benzamide with ethyl and pyridylmethyl on N, and two OCH₂CF₃ groups on benzene ring] | oil |

Other novel intermediates of the invention prepared according to the method of Example 1 are shown in Table II with the intermediates utilized in their preparation.

TABLE II

| Ex. No. | Formula II | Formula III | Product |
|---|---|---|---|
| 7 | [4-OCH₂CF₃, 3-OCH₂CF₃ benzoyl chloride] | HN(CH₂CH₃)—(1-methylpyrrol-2-yl) | [N-ethyl-N-(1-methylpyrrol-2-yl) 3,4-bis(OCH₂CF₃)benzamide] |
| 8 | 2,6-bis(OCH₂CF₃)-4-(OCH₂CF₃) benzoyl chloride | 2-(N-methylaminomethyl)pyridine | [N-methyl-N-(2-pyridylmethyl) 2,4,6-tris(OCH₂CF₃)benzamide] |
| 9 | 2-OCH₂CF₃, 4-OCH₂CF₃ benzoyl chloride | HN(CH₃)—CH(CH₃)—(2-pyridyl) | [N-methyl-N-(1-(2-pyridyl)ethyl) 2,4-bis(OCH₂CF₃)benzamide] |
| 10 | 2-OCH₂CF₃ benzoyl chloride | CH₃CH₂NHCH₂-(4-methylpyridin-2-yl) | [N-ethyl-N-((4-methylpyridin-2-yl)methyl) 2-OCH₂CF₃ benzamide] |
| 11 | 2-OCH₂CF₂CF₃ benzoyl chloride | 2-(CH₂NH-CH₂CH₂CH₃)pyridine | [N-propyl-N-(2-pyridylmethyl) 2-OCH₂CF₂CF₃ benzamide] |

The following example illustrates the reduction of intermediates of Formula IV to provide compounds of the invention of Formula I.

EXAMPLE 12

2,5-Bis(2,2,2-trifluoroethoxy)-N-methyl-N-(2-pyridylmethyl)benzamide (0.015 mole, 6.33 g.) in 200 ml. of glacial acetic acid is mixed with 0.2 g. of platinum oxideacetic acid paste and the mixture is shaken on a Parr hydrogenation apparatus at a temperature of about 23° C. for about 3.5 hours. The resulting material is filtered and the filtrate is evaporated, toluene being added to form an azeotrope and facilitate evaporation. The residue of the evaporation is mixed with 5 percent sodium hydroxide solution and diethyl ether, and the organic layer is separated, washed with saturated sodium chloride solution, dried and evaporated to provide a white solid, 2,5-bis(2,2,2-trifluoroethoxy)-N-methyl-N-(2-piperidylmethyl)benzamide, m.p. 104°–107° C.

The compounds of the examples of Table III are prepared according to the method generally described in Example 12.

TABLE III

| Ex. No. | Product |
|---|---|
| 13 | 2,5-bis(2,2,2-trifluoroethoxy)-N-ethyl-N-(2-piperidylmethyl)benzamide, m.p. 93–96° C. Analysis: %C %H %N  Calculated for $C_{19}H_{24}F_6N_2O_3$: 51.6 5.5 6.3  Found: 51.7 5.5 6.3 |
| 14 | 2,5-bis(2,2,2-trifluoroethoxy)-N-t-butyl-N-(2-piperidylmethyl)benzamide, b.p. 190° C/ 0.2 mg Hg. Analysis: Calculated for $C_{21}H_{28}F_6N_2O_3$: 53.6 6.0 6.0  Found: 53.6 6.1 5.8 |

EXAMPLE 15

Using the method of Example 12 except omitting the treatment with sodium hydroxide, 4.64 g. of 2,5-bis(2,2,2-trifluoroethoxy)-N-n-butyl-N-(2-pyridylmethyl)benzamide is reduced to provide white solid product, 2,5-bis(2,2,2-trifluoroethoxy)-N-n-butyl-N-(2-piperidylmethyl)benzamide acetate, m.p. 119°–120° C.

| Analysis: | %C | %H | %N |
|---|---|---|---|
| Calculated for $C_{21}H_{28}F_6N_2O_3 \cdot C_2H_4O_2$: | 52.1 | 6.1 | 5.3 |
| Found: | 52.1 | 6.0 | 5.2 |

EXAMPLE 16

Using the method of Example 12, 7.0 g. of 2,5-bis(2,2,2-trifluoroethoxy)-N-cyclohexyl-N-(2-pyridylmethyl)benzamide is reduced to provide 2,5-bis(2,2,2-trifluoroethoxy)-N-cyclohexyl-N-(2-piperidylmethyl)benzamide as the free base. The base is dissolved in diethyl ether and added dropwise to 500 ml. of ether solution, saturated with fumaric acid. The precipitated product is collected by filtration, washed with ether, then recrystallized from a 5:1 ethyl acetate-isopropanol mixture. The product is 2,5-bis(2,2,2-trifluoroethoxy)-N-cyclohexyl-N-(2-piperidylmethyl)benzamide fumarate, m.p. 132°–135° C. (dec).

| Analysis: | %C | %H | %N |
|---|---|---|---|
| Calculated for $C_{23}H_{30}F_6N_2O_3 \cdot 0.86 \cdot C_4H_4O_4$: | 53.9 | 5.7 | 4.7 |
| Found: | 53.9 | 6.1 | 4.7 |

EXAMPLE 17

2,5-Bis(2,2,2-trifluoroethoxy)-N-methyl-N-[2-(6-methylpyridyl)methyl]benzamide (7.2 g., 0.0165 mole) in 200 ml. of acetic acid is added to a paste of 0.2 g. of platinum oxide in acetic acid, and the mixture is shaken on a Parr hydrogenation apparatus at about 23° C. for five hours. The mixture is filtered, then evaporated, adding toluene to form an azeotrope and to facilitate evaporation. The residue hardens to a waxy beige solid and is triturated with diisopropyl ether to provide a white granular solid. Recrystallization from methyl isobutyl ketone gives 2,5-bis-(2,2,2-trifluoroethoxy)-N-methyl-N-[2-(6-methylpiperidyl)methyl]benzamide acetate, m.p. 130°–131° C.

| Analysis: | %C | %H | %N |
|---|---|---|---|
| Calculated for $C_{19}H_{24}F_6N_2O_3 \cdot C_2H_4O_2$: | 50.2 | 5.6 | 5.6 |
| Found: | 50.5 | 5.6 | 5.5 |

EXAMPLE 18

Using the method of Example 15, 5.8 g. of 2,5-bis-(2,2,2-trifluoroethoxy)-N-methyl-N-(2-pyridylmethyl)-benzamide is reduced to produce the white solid, 2,5-bis(2,2,2-trifluoroethoxy)-N-methyl-N-(2-piperidylmethyl)benzamide acetate, m.p. 113°–115° C.

| Analysis: | %C | %H | %N |
|---|---|---|---|
| Calculated for $C_{18}H_{22}F_6N_2O_3 \cdot C_2H_4O_2$: | 49.2 | 5.4 | 5.7 |
| Found: | 49.4 | 5.4 | 5.6 |

Using the method of Example 12, the following compounds are prepared from intermediates of Table II.

TABLE IV

| Ex. No. | Product |
|---|---|
| 19 | (structure: benzamide with $CF_3CH_2O$ groups at 2,5 positions; N-ethyl (CH₂CH₃); N-CH linked to pyrrolidine ring with CH₃ substituent) |
| 20 | (structure: 2,5-bis(trifluoroethoxy)benzamide; N-CH₃; N-CH₂-piperidine) |
| 21 | (structure: 2,5-bis(trifluoroethoxy)benzamide; N-CH₂CH₃; N-CH₂-4-methylpiperidine) |

TABLE IV-continued

| Ex. No. | Product |
|---|---|
| 22 | CH₃CH₂CH₂ group with O=C-N-CH₂ linked to piperidine-NH and phenyl-OCH₂CF₂CF₃ |
| 23 | CH₃, CH₃ substituted O=C-N-CH linked to piperidine-NH, with phenyl bearing CF₃CH₂O and OCH₂CF₃ |

EXAMPLE 24

To a mixture of 2.9 g. (0.0203 mole) of 1-methyl 2-(N-ethylaminomethyl)pyrrolidine and 8.6 g. (0.0814 mole) of sodium carbonate in 150 ml. of benzene is added dropwise over about 1.5 hours a solution of 6.86 g. (0.0203 mole) of 2,5-bis-(2,2,2-trifluoroethoxy)benzoyl chloride in 35 ml. of benzene. The mixture is stirred for 65 hours, then heated at reflux temperature for five hours. The mixture is evaporated, the residue is partitioned between dichloromethane and water, then with saturated sodium chloride solution, and dried. The solution is concentrated and the residue is distilled under vacuum to provide 2,5-bis(2,2,2-trifluoroethxy)-N-ethyl-N-[2-(1-methylpyrrolidyl)methyl]benzamide, b.p. 163°C/0.22 mm Hg.

| Analysis: | %C | %H | %N |
|---|---|---|---|
| Calculated for $C_{19}H_{24}F_6N_2O_3$: | 51.5 | 5.5 | 6.3 |
| Found: | 51.3 | 5.7 | 6.2 |

What is claimed is:

1. A compound of the formula

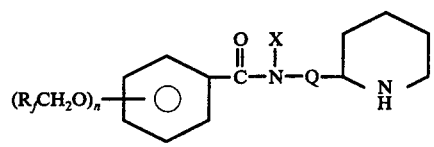

wherein $R_f$ is a perfluoroalkyl radical containing one to three carbon atoms, $n$ is one to three, Q is methylene or methylmethylene and X is a cycloalkyl group containing five or six carbon atoms or a pharmaceutically acceptable salt thereof.

2. The compound 2,5-bis(2,2,2-trifluoroethoxy)-N-cyclohexyl-N-(2-piperidylmethyl)benzamide or a pharmaceutically acceptable salt thereof.

* * * * *